(12) United States Patent
Webb et al.

(10) Patent No.: US 6,303,128 B1
(45) Date of Patent: Oct. 16, 2001

(54) METHOD FOR PROTEIN EXPRESSION

(75) Inventors: Elizabeth Ann Webb, Eltham; Stirling John Edwards, Northcote, both of (AU)

(73) Assignee: CSL Limited, Victoria (AU)

(*) Notice: Subject to any disclaimer, the term of this patent is extended or adjusted under 35 U.S.C. 154(b) by 0 days.

(21) Appl. No.: 09/358,645

(22) Filed: Jul. 23, 1999

Related U.S. Application Data

(63) Continuation-in-part of application No. 08/860,165, filed as application No. PCT/AU95/00868 on Dec. 20, 1995, now Pat. No. 6,004,557.

(30) Foreign Application Priority Data

Dec. 20, 1994 (AU) .............................. PN 0157/94

(51) Int. Cl.⁷ .................. A61K 39/12; A61K 39/00; C12N 15/00
(52) U.S. Cl. .................... 424/199.1; 424/192.1; 435/320.1; 435/325; 435/235.1; 435/69.1; 435/69.7
(58) Field of Search ............... 424/199.1, 192.1; 435/320.1, 235.1, 69.1, 325, 69.7

(56) References Cited

U.S. PATENT DOCUMENTS

| | | | |
|---|---|---|---|
| 5,719,054 | 2/1998 | Boursnell et al. | 435/320.1 |
| 6,010,875 | * 1/2000 | Fischer | 435/69.1 |

FOREIGN PATENT DOCUMENTS

| | | |
|---|---|---|
| 76212/91 | 11/1991 | (AU) . |
| 92/05248 | 4/1992 | (WO) . |
| 92/10513 | 6/1992 | (WO) . |
| 9 216 636 | 10/1992 | (WO) . |

OTHER PUBLICATIONS

Stoeppler et al., "Transforming Proteins of The Papillomaviruses", *Invervirology*, vol. 37:168–179, (1994).

* cited by examiner

*Primary Examiner*—Ali R. Salimi
(74) *Attorney, Agent, or Firm*—Foley & Lardner

(57) ABSTRACT

A vector system for expressing foreign proteins or polypeptides in bacteria such as *E. coli* is disclosed. The vector system is especially useful in obtaining expression of non-transforming variants of human papilloma virus antigens.

12 Claims, 4 Drawing Sheets

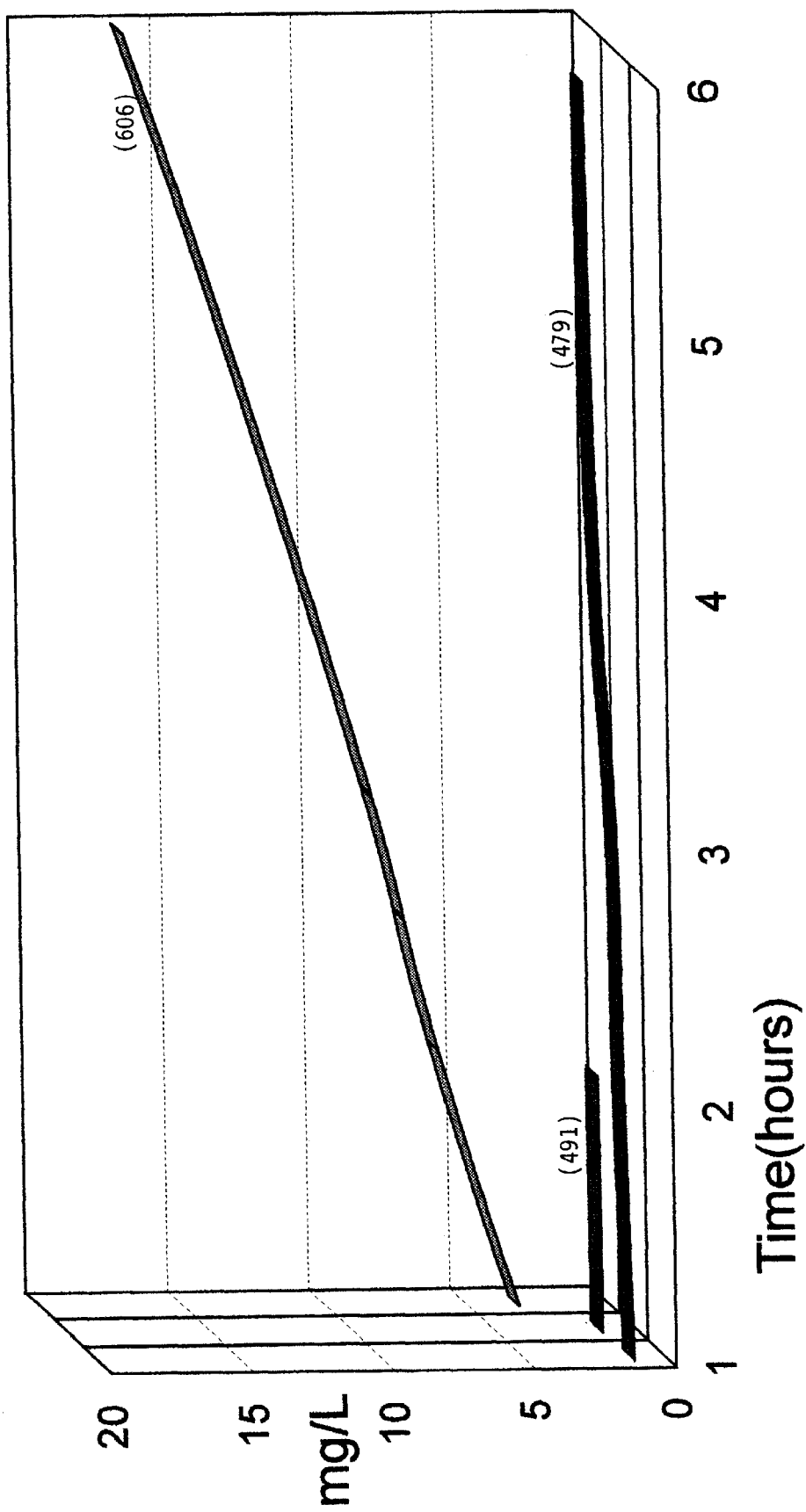

SEQUENCE LISTING

```
<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 1
cgctcgagag atctcatatg caccaaaaga gaactgc                              37

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 2
cgcccgggca gctgggtttc tctacgtg                                        28

<210> SEQ ID NO 3
<211> LENGTH: 36
```

```
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 3
cgcccgggat gcatggagat acacctacat tgcatg                            36

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 4
cggtcgacgg atcctggttt ctgagaacag atggg                             35

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 5
gcgcgaattc tattaaggag cccgggatgg ggaatccata tgctgtat               48

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 6
cgcgagatct ccgaagcgta gagtcacact tg                                32

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 7
cgcccgggta atgttgttcc atacaaacta                                   30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide used for PCR amplification

<400> SEQUENCE: 8 cgcccggga ggaggaggat gaaatagatg                                    30

<210> SEQ ID NO 9
<211> LENGTH: 49
<212> TYPE: DNA
```

-continued

```
<213> ORGANISM: Artificial Sequence
<220> FEATURE:
<223> OTHER INFORMATION: Description of Artificial Sequence: PCR Primer

<400> SEQUENCE: 9
gcgcgaattc tattaaggag cccgggatgg ggaatccata tgctgtatg          49

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: PCR Primer

<400> SEQUENCE: 10
cgcgagatct ccgaagcgta gagtcacact tg                             32

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence:
      Phosphorylated linker

<400> SEQUENCE: 11
tgctctagag ca                                                   12

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: expression
      vector

<400> SEQUENCE: 12
tggtgctcta gagcacca                                             18
```

METHOD FOR PROTEIN EXPRESSION

CROSS-REFERENCE TO RELATED APPLICATIONS

This application is a continuation-in-part of U.S. application Ser. No. 08,860,165, filed Sep. 22, 1997, now U.S. Pat. No. 6,004,557, the contents of which are incorporated herein by reference. U.S. application Ser. No. 08/860,165 corresponds to 371 International Patent Application No. PCT/AU95/00868 (WO96/19496), filed Dec. 20, 1995.

FIELD OF THE INVENTION

This invention relates to an improved method for protein expression, particularly in bacteria such as *Escherichia coli*. In particular, this invention relates to an improved expression vector system and to the use of this system to obtain expression of foreign proteins or polypeptides in bacteria such as *E. coli*. By way of example, the improved expression vector system may be used to obtain expression of non-transforming variants of human papilloma virus (HPV) antigens as disclosed in detail in International Patent Application No. PCT/AU95/00868.

BACKGROUND OF THE INVENTION

In International Patent Application No. PCT/AU88/00164, it is disclosed that a fusion protein having a foreign protein or polypeptide component fused to the enzyme glutathione-S-transferase (GST), (E.C. 2.5.1.18), preferably to the carboxy-terminal of the enzyme, avoids several of the difficulties associated with known fusion proteins, for instance fusions wherein the foreign protein or polypeptide is expressed as a fusion with *E. coli* β-galactosidase, in that the GST fusion proteins are generally soluble and can be purified from bacterial lysates under non-denaturing conditions, for example by affinity chromatography on a column of immobilised glutathione. The GST enzyme in the fusion protein may be derived from the parasite helminth *Schistosoma japonicum*, or it may be derived from other species including humans and other mammals.

The GST fusion proteins disclosed in International Patent Application No. PCT/AU88/00164 may be used as such, since the foreign protein or polypeptide component thereof often retains its antigenicity and functional activity. Alternatively, the fusion protein may be cleaved to provide the foreign protein or polypeptide as a synthesis product, and when the production of such a synthetic protein or polypeptide is desired a cleavable link may be provided in the fusion protein between the glutathione-S-transferase component and the foreign protein or polypeptide component. The cleavable link is preferably one which can be cleaved by a site-specific protease such as thrombin, blood coagulation Factor Xa, or the like.

Expression vectors for use in the expression of such GST fusion proteins are now available commercially and are known as "pGEX vectors". A pGEX vector is an expression vector, more particularly a bacterial plasmid for use in the production of a foreign protein or polypeptide, wherein the vector has inserted therein a nucleotide sequence capable of being expressed as the glutathione-S-transferase enzyme followed by at least one restriction endonuclease recognition site for insertion of a nucleotide sequence capable of being expressed as a foreign protein or polypeptide fused with the COOH-terminus of the glutathione-S-transferase enzyme, optionally with a sequence capable of being expressed as a cleavable link between the enzyme and the foreign protein or polypeptide.

Expression of the GST fusion proteins by the pGEX expression vectors is under the control of the tac promoter which enables inducible, high-level production of these fusion proteins. The pGEX expression vectors also contain the lac Iq gene, so that they can be used in any *E. coli* strain.

Polypeptides expressed in *E. coli* as fusions with GST have proven useful for the analysis of protein-DNA and protein-protein interactions. Part of the reason for this is that, in contrast to many other expression systems, the purification of GST fusion proteins involves non-denaturing conditions so that the expressed polypeptide is recovered in a relatively native state and retains at least some of its normal properties.

The present invention provides an improved expression vector system based on the pGEX expression vectors described above, which retains the high expression characteristics of this system but yields a protein product that is not a GST fusion. Thus, the system of this invention has an advantage over the existing pGEX technology in that a high yield of a "native" protein can be obtained without the necessity to cleave away the GST enzyme moiety of a GST fusion protein. This is especially useful where it is demonstrated that GST does not function as a purification aid.

SUMMARY OF THE INVENTION

In accordance with this invention, there is provided an expression vector having inserted therein a recombinant nucleotide sequence operatively linked to an expression control sequence, said recombinant nucleotide sequence comprising, in the 5' to 3' direction:

(i) a first nucleotide sequence which encodes a glutathione-S-transferase (GST) enzyme, said first nucleotide sequence including a termination codon in frame with the GST initiation codon to truncate the protein or polypeptide expressed by said first nucleotide sequence; and (ii) a second nucleotide sequence comprising at least one restriction endonuclease recognition site for insertion of a further nucleotide sequence capable of being expressed as a desired protein or polypeptide.

In another aspect, the invention provides an expression vector as broadly described above, wherein the recombinant nucleotide sequence further comprises:

(iii) a third nucleotide sequence comprising a ribosome binding site (RBS) sequence, said third nucleotide sequence being located between said first nucleotide sequence and said restriction endonuclease recognition site.

In yet another aspect, the present invention provides an expression vector as broadly described above, wherein the recombinant nucleotide sequence further comprises:

(iv) a further nucleotide sequence capable of being expressed as a desired protein or polypeptide inserted into said restriction endonuclease recognition site.

In yet another aspect, there is provided a host cell, particularly a prokaryotic host cell such as *E. coli*, transformed with an expression vector as broadly described above.

The present invention also extends to a method for production of a desired protein or polypeptide, which comprises the step of culturing host cells as broadly described above under conditions such that the desired protein or polypeptide is expressed in recoverable quantity, and optionally the further step of recovering the desired protein or polypeptide from the cell culture.

The GST enzyme expressed by the first nucleotide sequence may be derived from *Schistosoma japonicum*, or it may be derived from other species including humans and other mammals.

The precise nature of the desired protein or polypeptide which may be expressed in accordance with this invention is not essential. Accordingly, the present invention extends to the production of any polypeptide or protein of interest as the desired protein or polypeptide. By way of example, this polypeptide or protein of interest may be a particular antigen to be used for diagnostic or therapeutic purposes in the human or veterinary fields.

The RBS sequence which is provided "upstream" of the restriction endonuclease recognition site(s) in the expression vector of this invention may be any known ribosome binding site. By way of example, the ribosome binding site sequence may comprise the AGGAG sequence, or the consensus sequence TAAGGAGG required for binding to $16^S$ ribosomal RNA.

Preferably, the expression control sequences in the expression vectors of the present invention are the same as in the pGEX expression vectors.

DETAILED DESCRIPTION OF THE INVENTION

GST fusion proteins derived from pGEX expression vectors have been in widespread use since 1988. The pGEX expression system has proved to be a reliable way of producing certain proteins in quantity and the presence of GST in the fusion protein provides a means of purification using glutathione affinity chromatography. However, in a number of cases GST fusion proteins have proven to be difficult to purify using this method. This has led researchers to investigate alternative means of purifying these fusion proteins. As well, even in the case where purification on glutathione is practical, the protein product retains a GST moiety which in many cases is undesirable. In order to overcome this limitation, some pGEX vectors contain proteolytic cleavage sites between GST and the protein of interest, allowing cleavage away of the GST using the appropriate protease (such as thrombin in the case of the pGEX-4T-1 vector). However, such methodology is problematical in that cleavage may not be specific and such technology is difficult to apply at industrial scale. As well, the use of agents such as thrombin may be undesirable in the production of proteins destined for human therapeutic use.

One advantage of the pGEX expression vector is that production levels of proteins which alone are poorly expressed in E. coli can be markedly increased by linkage to GST. One explanation for this observation is that the increased size of messenger RNA coding for the fusion protein leads to enhanced protein production by increased messenger RNA stability.

The present invention combines the putative advantages of messenger stability leading to enhanced protein levels, with a removal of the requirement for fusion protein cleavable characteristic of the pGEX expression vector system.

This invention provides for the high level production of any protein in E. coli and is useful for the large scale production of proteins for use as human therapeutic agents and other applications. Laboratory evidence indicates that proteins which are produced poorly in other vector systems but which are produced at useful levels as GST fusion proteins are produced at similar levels to the latter by the use of the expression vectors of the present invention. Experimental evidence also suggests that proteins engineered to contain hydrophobic sequences, which would be expected to be poorly produced in E. coli , are synthesised at useful levels in accordance with the present invention. pGEX vector DNA (AMRAD/Pharmacia) was manipulated so as to result in truncation of the glutathione-S-transferase coding region at an early point in synthesis by the insertion of a termination codon. Thus, while the size of the messenger RNA remain unchanged, glutathione-S-transferase could not be incorporated into a fusion protein. To produce a desired or foreign protein in this new vector, it was necessary to also insert a ribosome binding site upstream of the gene of interest.

To facilitate the insertion of a termination codon, use was made of a convenient, unique restriction site (BalI) at position 463 (GST initiation codon is at position 258) to create a blunt-ended DNA molecule. Into this site was cloned a 12-mer XbaI phosphorylated linker (Promega Corporation) which would introduce the "in frame" termination codon, to create the vector pGEX STOP. This vector has been deposited under the terms of the Budapest Treaty with the Australian Government Analytical Laboratory, Pymble, New South Wales, Australia, and given accession number NM01/19536.

To allow expression of a protein coding for HPV 16 early genes E6 and E7 in pGEX STOP these E6 and E7 sequences were removed from pDS56 (Roche), in addition to upstream sequences containing a RBS, by cleavage with EcoRI and HindIII (which was then blunted) and inserted into polylinker sites EcoRI/SmaI in the vector pGEX STOP. Expression of the E6/E7 fusion protein in this system resulted in a significant improvement in protein production over that obtained from the Roche pDS56 vector system.

Further details of the present invention are illustrated by way of example only, in the following Example and in the accompanying Figures.

In the Figures:

FIG. 4 shows expression quantities of E6/E7/His6 fusion proteins in three different systems pDS56, pGEX STOP2 and pET23b.

EXAMPLE 1

A. GENERAL (i) Insertion of a termination codon into the GST coding sequence of pGEX-4T-1.

Figure 1:
FIG. 1 shows the preparation of the expression vector pGEX STOP (FIGS. 1a to 1c, SEQ ID No: 12), and insertion of a RBS and HPV16 E6 and E7 sequences (FIGS. 1d to 1f).
Figure 1:
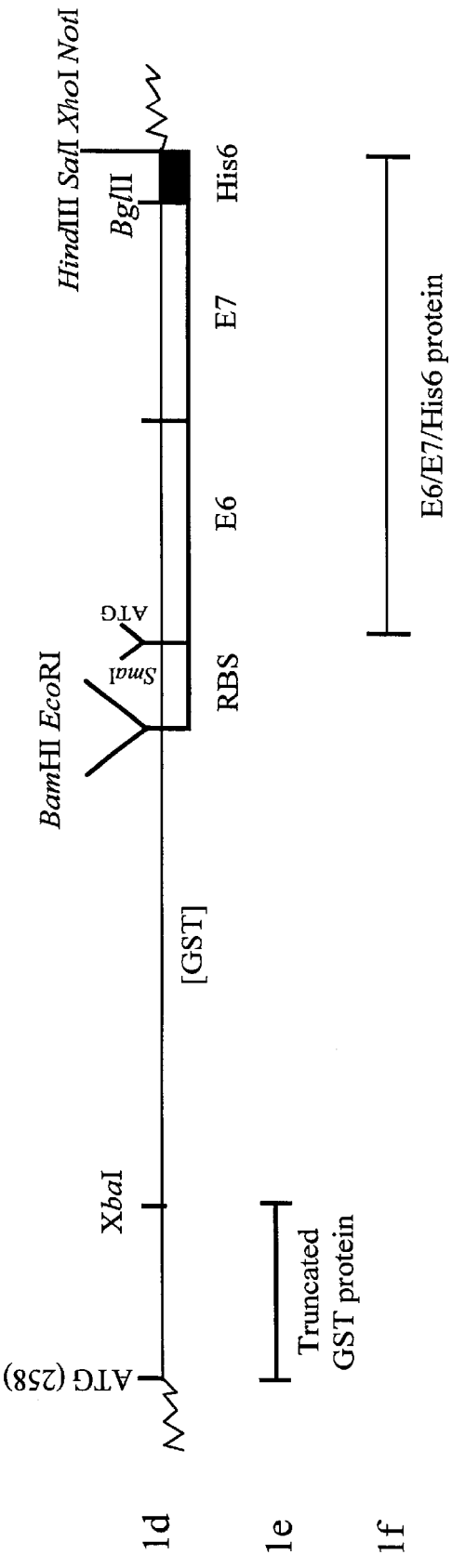

Use was made of a unique BalI site 205 base pairs downstream from the GST initiation codon of pGEX-4T-1 (AMRAD/Pharmacia) (FIG. 1a). Cleavage at this site created a blunt-ended molecule (FIG. 1b) into which was cloned a 12-mer XbaI phosphorylated linker supplied by Promega Corporation (SEQ ID No: 11) (5'TGCTCTAGAGCA3') (FIG. 1c). This introduced an XbaI site into pGEX-4T-1 where previously none was present and hence cleavage by XbaI indicated successful incorporation of the linker into the pGEX-4T-1 sequence to create the vector pGEX STOP.

The linker sequence provided an in-frame termination codon (TAG) which would cause the GST protein to be truncated at this point (FIG. 1e).

(ii) Introduction of a RBS upstream of the foreign gene.

To allow expression of a foreign gene inserted into the multiple cloning site of pGEX, a ribosome binding site (RBS) sequence was introduced upstream of an initiation codon. This was achieved by removing a cassette containing the RBS sequence (AGGAG), HPV16 E6 and E7 sequences fused in-frame and a polyhistidine sequence from pDS56 (Roche) (EcoRI/HindIII fragment) for insertion via intermediate cloning steps into the EcoRI/SalI sites of pGEX-4T-1 (FIG. 1d), thus allowing production of an E6/E7/His6 fusion protein from pGEX STOP (FIG. 1f).

(iii) Expression of an E6/E7/His6 fusion protein.

Protein levels produced by three different systems were compared: E6/E7/His6 from pDS56 (Roche), GST/E6/E7/His6 from pGEX-4T-1 (AMRAD/Pharmacia) and E6/E7/His6 from pGEX STOP. In each of these systems transcription is controlled by the IPTG inducible tac promoter.

Plasmid DNA was transformed into appropriate *E.coli* strains (SG13009 and MI5 for pDS56, TOPP2 or BL21 for pGEX-4T-1 and pGEX STOP) and cultures grown, with samples obtained three hours post-induction for analysis in SDS-PAGE and either Coomassie Blue staining or Western blotting with an anti-E7 antibody.

B. Materials and Methods

Cloning and expression of GST/E6/E7/His6 fusion protein.

In order to prepare a molecule consisting of HPV-16 E6 and E7 sequences as an "in-frame" fusion, a clone of HPV-16 DNA containing both E6 and E7 genomic sequences was used as the template for separate PCR amplification of E6 and E7 using oligonucleotides:

(i) for E6:
(a) (5')CGCTCGAGAGATCTCATATGCACCAAAAG AGAACTGC(3') (SEQ ID NO:1) and
(b) (5')CGCCCGGGCAGCTGGGTTTCTCTACGTG(3') (SEQ ID NO:2); and (ii) for E7:
(c) (5')CGCCCGGGATGCATGGAGATACACCTACAT TGCATG(3') (SEQ ID NO:3) and
(d) (5')CGGTCGACGGATCCTGGTTTCTGAGAACAG ATGGG(3') (SEQ ID NO:4).

A SmaI recognition site at the 3' end of E6 and the 5' end of E7 facilitated the fusion and introduced two additional amino acids (proline and glycine) between E6 and E7. Additional restriction enzyme recognition sites at the 5' and 3' boundaries of the fusion molecule (introduced in the oligonucleotides) aided in subsequent cloning procedures.

The fused E6 /E7 sequence was cloned as a BglII-BamHI fragment into vector pDS56 (Stuber et al., (1990). In *Immunological Methods*, Vol. IV, Eds. Lefkovits, I. and Pernis, B., Academic Press, 121–152) which provided an in-frame 3' hexa-his(His6) sequence. From this, E6/E7/His6 was removed as a EcoRI/Hind III fragment and subcloned into pGEM 7+3, which was created by inserting the BamHI/HindIII portion of the pGEM3-Zf(+)(Promega) polylinker into the BamHI/HindIII site of the multiple cloning site of the pGEM7-Zf(+)(Promega) vector. E6/E7/His6 was then removed from pGEM7+3 as a EcoRI/Sal I fragment and inserted into the multiple cloning site of pGEX-4T-1 (AMRAD/Pharmacia) to produce pGEX-4T-1 E6/E7/His6. This plasmid was used to transform a variety of *E. coli* strains including TOPP2 (Stratagene) and BL21 (AMRAD/Pharmacia). Both types of transformed cells produced a significant amount of fusion protein following IPTG induction. The fusion protein (GST/E6/E7/His6) was in the expected size range of around 60 kDa. The identity of the protein was confirmed by Western blots probed with two monoclonal antibodies directed against E7 (LHIL.16E7.8F and LHIL.16E7.6D, Tindle et al (1990) *Journal of General Virology*, 71:1347–1354).

II Cloning and expression of E6/E7/His6 fusion protein

In order to express E6/E7/His6 as protein lacking GST, a termination codon was introduced into pGEX-4T-1 E6/E7/His6 at a unique BalI site 3' to, and in-frame with, the GST translation initiation codon using the phosphorylated linker, (SEQ ID NO: 11) TGCTCTAGAGCA. After transforming *E. coli* strain BL21 with this new plasmid ([GST] E6/E7/His6) a significant amount of protein (E6/E7/His6) was produced following IPTG induction at a size of approximately 33 kD which corresponds to the size expected of a E6/E7/His6 fusion protein. Identity of this protein was confirmed by Western blot using the same monoclonal antibodies directed against E7 as described above.

C. Results

Figure 2A:
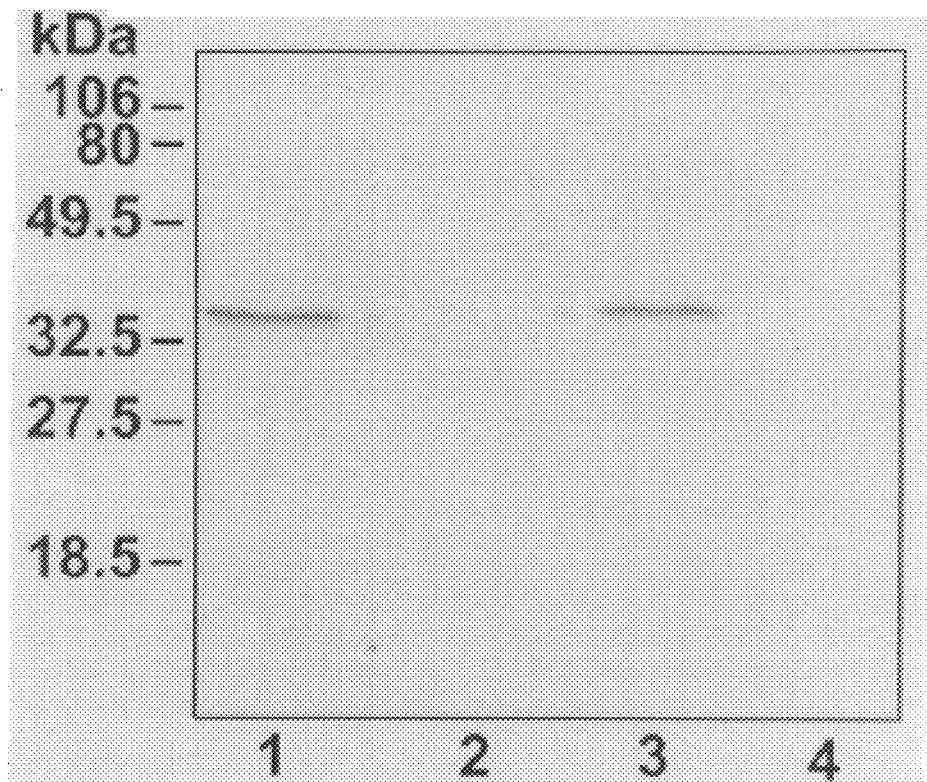
FIGS. 2 and 3 show expression of the E6/E7/His6 fusion protein (approx. 36 kDa) in the three different systems pDS56 (Roche), pGEX-4T-1 (AMRAD/Pharmacia) and pGEX STOP, respectively.
Figure 2B:
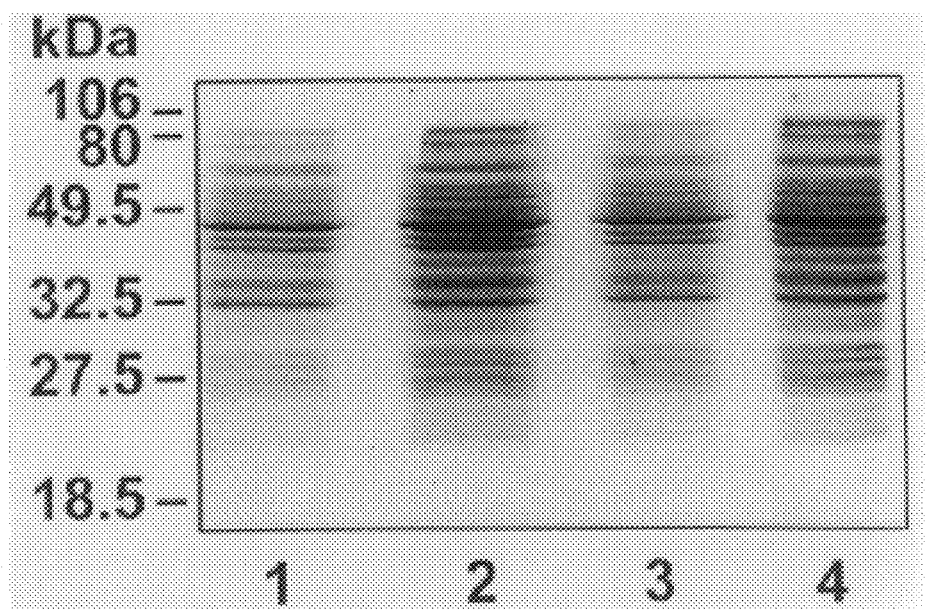
Figure 3A:
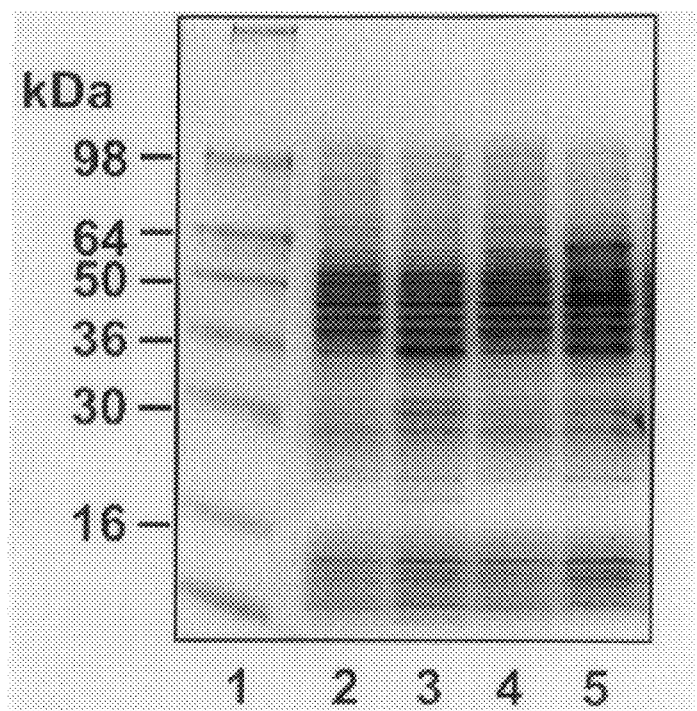
Figure 3B:
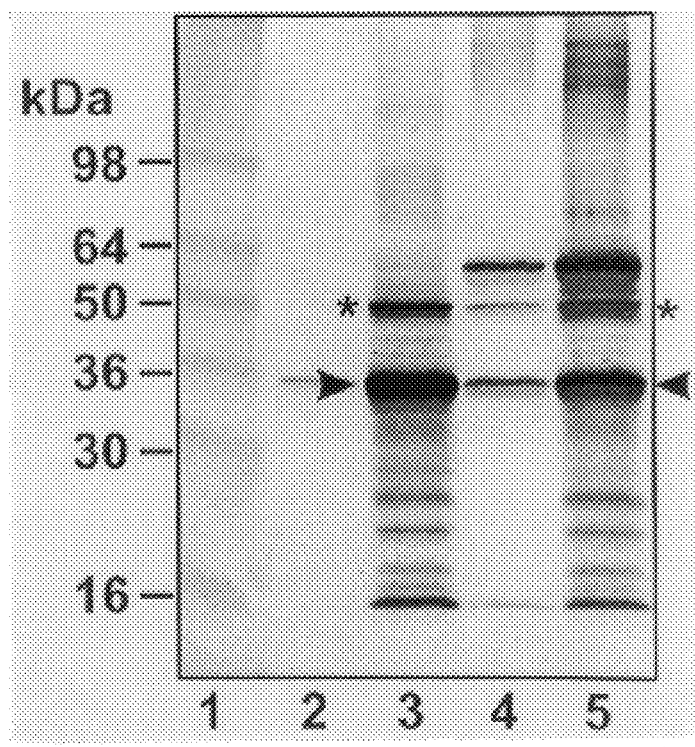

While the pDS56 vector allowed the production of some protein as detected by a Western blot of induced samples (FIG. 2A, lanes 1 (SG13009) and 3 (M15)) compared with uninduced samples (FIG. 2A, lanes 2 and 4), there was no equivalent band in a Coomassie stained gel (FIG. 2B) indicating that only a small amount of protein was present. However, when E6/E7/His6 was produced as a fusion protein with GST from the pGEX-4T-1 vector in BL21 cells, the protein could easily be visualised with Coomassie staining of induced samples (FIG. 3A, lane 5) compared with uninduced samples (FIG. 3A, lane 4). The presence of the E6 E7 sequence was confirmed by immunoblotting (FIG. 3B, lane 5).

Importantly, this same increased level of protein was also evident for E6/E7/His6 produced both in this system and without GST in the pGEX STOP vector (arrows, FIG. 3B), demonstrating a marked difference from earlier attempts to produce this protein. FIGS. 3A, lane 3 and 3B, lane 3 show the results obtained with Coomassie staining and Western blotting respectively for the pGEX STOP vector.

Since the mRNA transcript produced from pGEX-4T-1 and pGEX STOP (each containing E6 /E7 /His6) should be almost identical, it is possible that the similar high levels of protein (either GST/E6/E7/His6 or E6 /E7 /His6) may result from the increased stability of this long mRNA molecule in comparison with the much shorter transcript produced when E6 /E7/His6 is produced in the pDS56 expression system.

EXAMPLE 2

Cloning and Expression of Deleted (non-full length) Forms of HPV E6 and E7

(i) Construction of ΔE6 C/ΔE7 N

Full length HPV E6 /E7 in pGEM3(Promega) served as a template for PCR amplification of deleted forms of E6 /E7 using oligonucleotides 5'GCGCGAATTCTAT TAAGGAGCCCGGGATGGGGAATCCATATGCTGTAT3' (SEQ ID NO:5) and 5'CGCGAGATCTCC GAAGCGTAGAGTCACACTTG3'(SEQ ID NO: 6).

The resulting truncation of E6 /E7 lacking sequences at the N terminal of E6 (189 bp) and C terminal of E7 (96 bp) was subcloned into pGEX-4T-1 containing a termination codon in the GST sequence as described in Example 1 to produce [GST] ΔE6 C/ΔE7 N/His6. This plasmid was used to transform *E. coli* strain BL21. Transformed cells expressed a significant amount of fusion protein (ΔE6C/ΔE7N/His6), following IPTG induction producing a protein of the approximate expected size (20 kD). The identity of this protein was confirmed by Western blot using the same monoclonal antibodies as in Example 1.

(ii) Construction of ΔE7 C/ΔE6N

Using oligonucleotides (a) in Example 1 (SEQ ID NO: 1) and 5'CGCCCGGGTAA-TGTTGTTCCATACAAACTA3'

(SEQ ID NO: 7), an N-terminal representation of E6 comprising 285 bp was amplified from the same HPV-16 clone utilised in Example 1. As well, oligonucleotides 5'CGCCCGGGGAGGAGGAGGATGAAATAGATG3' (SEQ ID NO: 8) and (d) in Example 1 (SEQ ID NO: 4) were used to produce a 198 bp C-terminal E7 sequence. These were each blunt cloned into pGEM7-Zf(+) (Promega). A fusion cassette was formed by restricting the E6 clone with Kpnl/BglII and inserting the E7 sequence upstream as a Kpnl/BamHI fragment. This fused sequence was then reamplified with SmaI and Bg/II cloning sites for insertion into pGEX-4T-1 containing a termination codon in the GST sequence as described in Example 1 to produce [GST] ΔE7 C/ΔE6 N/His6. After transformation into *E. coli* BL21, protein production was assayed by PAGE followed by Coomassie staining and Western blotting. A protein ΔE7 C/ΔE6 N/His6), of the expected size (20 kD) was evident on Western blots.

EXAMPLE 3

A. Materials and Methods pGEX STOP as described in Example 1 was further improved by exchanging the existing RBS with an improved consensus sequence TAAGGAG which also included a stretch of upstream pyrimidine residues. At the same time, the distance between the RBS and initiation codon was reduced to the more ideal situation of six residues and this sequence was engineered to contain a SmaI restriction site for cloning purposes.

To achieve this, PCR primers containing these sequence changes (forward 5'GCGCGAATTC TATTAAGGAGC CCGGGATGGGGAATCCATATGCTGTATG3'-SEQ ID NO: 9, and reverse 5'CGCGAGATCTCCGAAGCGTAGA GTCACACTTG3'-SEQ ID NO: 10) were utilised to amplify a HPV 16 E6 E7 fusion protein which contained 5' and 3' deletions. This product was recloned into the EcoRI/BglII sites of pGEX STOP (FIG. 1*d*) to yield the vector pGEX STOP2. This vector has been deposited under the terms of the Budapest Treaty with the Australian Government Analytical Laboratory, Pymble, New South Wales, Australia, and given accession number NM01/19537.

To investigate the expression levels of the full length E6 /E7 /His6 fusion protein resulting from this change of RBS, the deletion variant of E6 /E7 was removed from pGEX STOP2 by SmaI and BglII digestion and replaced by a full-length E6 /E7 EcoRV/BglII fragment.

Protein levels expressed by three different systems were then compared E6/E7/His6 from pDS56 (Roche) (discussed in Example 1), from pGEX STOP2 and from pET23b (a vector from Novagen which utilises the T7 promoter). In the former two vector systems, transcription is controlled by the IPTG inducible tac promoter.

Plasmid DNA was transferred into the appropriate *E. coli* strains. These were MI5 (Stuber et al., 1990, ibid) for pDS56, BL21 (Stratagene) for pGEX STOP2 and BL21 (DE3) (Novagen) for pET23b. Cultures were grown to $A_{600}$~1 and induced with 1 mM IPTG. Samples were removed at 1, 2, 3 and 6 hours [pDS56 (479) and pGEX STOP2 (606)] and 1 and 2 hours [pET23b (491)].

The samples were assessed by an HPV 16 E6 /E7 -specific solid phase enzyme immunoassay (EIA) (Edwards et al. (1998) *Recent Res. Devel. in Biotech. and Bioeng.* 1, 343–356).

Results

The results shown in FIG. 4 indicate that after 2–3 hours induction virtually no increase in protein production occurred with levels of around 2 mg/litre being achieved for both the pDS56 and pET23b systems. However, for pGEX STOP2, a level of 16 mg/litre was obtained after 6 hours induction and other data (not shown) indicated that overnight induction led to levels of approximately 25 mg/litre.

What is claimed is:

1. An expression vector having inserted therein a recombinant nucleotide sequence operatively linked to an expression control sequence, said recombinant nucleotide sequence comprising, in the 5' to 3' direction:
   i. a first nucleotide sequence which encodes a glutathione-S-transferase (GST) enzyme, said first nucleotide sequence including a termination codon in frame with the GST initiation codon to truncate the protein or polypeptide expressed by said first nucleotide sequence; and
   ii. a second nucleotide sequence comprising at least one restriction endonuclease recognition site for insertion of a further nucleotide sequence capable of being expressed as a desired protein or polypeptide.

2. An expression vector according to claim 1, wherein the termination codon is included at the unique Ba/I site of the first nucleotide sequence.

3. An expression vector according to claim 1, wherein the recombinant nucleotide sequence further comprises:
   iii. a third nucleotide sequence comprising a ribosome binding site (RBS) sequence, said third nucleotide sequence being located between said first nucleotide sequence and said restriction endonuclease recognition site.

4. An expression vector according to claim 3, wherein the recombinant nucleotide sequence further comprises:
   iv. a further nucleotide sequence capable of being expressed as a desired protein or polypeptide inserted into said restriction endonuclease recognition site.

5. A host cell transformed with an expression vector according to claim 4.

6. A host cell according to claim 5, which is a prokaryotic host cell.

7. A host cell according to claim 6, which is *E. coli*.

8. The expression vector pGEX STOP.

9. The expression vector pGEX STOP2.

10. A host cell, transformed with an expression vector according to claim 8.

11. A host cell transformed with an expression vector according to claim 9.

12. A method for production of a desired protein or polypeptide, which comprises the step of culturing a host cell according to claim 5 under conditions such that the desired protein or polypeptide is expressed in recoverable quantity, and optionally recovering the desired protein or polypeptide from the cell culture.

* * * * *